(12) United States Patent
Shaw

(10) Patent No.: US 9,566,149 B2
(45) Date of Patent: Feb. 14, 2017

(54) DEVICES AND METHODS FOR IN SITU FENESTRATION OF A STENT-GRAFT AT THE SITE OF A BRANCH VESSEL

(75) Inventor: Edward E. Shaw, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 13/286,980

(22) Filed: Nov. 1, 2011

(65) Prior Publication Data

US 2012/0130478 A1 May 24, 2012

Related U.S. Application Data

(60) Provisional application No. 61/414,065, filed on Nov. 16, 2010.

(51) Int. Cl.
| | |
|---|---|
| *A61F 2/06* | (2013.01) |
| *A61F 2/07* | (2013.01) |
| *A61F 2/82* | (2013.01) |
| *A61F 2/89* | (2013.01) |
| *A61F 2/90* | (2013.01) |

(52) U.S. Cl.
CPC .. *A61F 2/07* (2013.01); *A61F 2/89* (2013.01); *A61F 2/90* (2013.01); *A61F 2002/061* (2013.01); *A61F 2002/068* (2013.01); *A61F 2002/821* (2013.01); *A61F 2220/0033* (2013.01); *A61F 2250/006* (2013.01); *A61F 2250/0023* (2013.01); *A61F 2250/0024* (2013.01); *A61F 2250/0039* (2013.01); *A61F 2250/0071* (2013.01); *A61F 2250/0096* (2013.01); *A61F 2250/0098* (2013.01)

(58) Field of Classification Search
CPC .................................................. A61F 2002/068
See application file for complete search history.

(56) References Cited

U.S. PATENT DOCUMENTS

| | | | |
|---|---|---|---|
| 5,219,335 | A | 6/1993 | Willard et al. |
| 5,281,203 | A | 1/1994 | Ressemann |
| 5,632,762 | A | 5/1997 | Myler |
| 5,951,599 | A | 9/1999 | McCrory |
| 5,984,955 | A | 11/1999 | Wisselink |

(Continued)

FOREIGN PATENT DOCUMENTS

| | | |
|---|---|---|
| EP | 1 487 380 | 2/2008 |
| WO | 02/15824 | 2/2002 |

(Continued)

OTHER PUBLICATIONS

International Search Report and Written Opinion from PCT/US2011/058948, mailed Nov. 16, 2010, 14 pages.

*Primary Examiner* — Jacqueline Woznicki

(57) ABSTRACT

The present disclosure includes a stent-graft comprising a first portion that is configured to engage a vessel wall, a second portion that is configured not to engage the vessel wall, and a perfusion window that is configured to permit blood flow. The stent-graft may further comprise a transition portion between the first portion and the second portion, and the perfusion window may be formed in the first portion, the second portion, and/or the transition portion. In a variety of embodiments, one of the first and the second portion may have a smaller diameter than the other. Similarly, in a variety of embodiments, the transition portion may be frustoconically shaped.

8 Claims, 6 Drawing Sheets

(56) References Cited

U.S. PATENT DOCUMENTS

| | | |
|---|---|---|
| 6,022,319 A | 2/2000 | Willard et al. |
| 6,066,100 A | 5/2000 | Willard et al. |
| 6,139,524 A | 10/2000 | Killion |
| 6,183,492 B1 | 2/2001 | Hart et al. |
| 6,245,100 B1 | 6/2001 | Davila et al. |
| 6,296,661 B1 | 10/2001 | Davila et al. |
| 6,372,995 B1 | 4/2002 | Mochizuki et al. |
| 6,432,127 B1 | 8/2002 | Kim et al. |
| 6,458,153 B1 | 10/2002 | Bailey et al. |
| 6,626,439 B1 | 9/2003 | Forry et al. |
| 6,652,567 B1 | 11/2003 | Deaton |
| 6,814,752 B1 | 11/2004 | Chuter |
| 6,949,121 B1 | 9/2005 | Laguna |
| 7,186,334 B1 | 3/2007 | Barnes |
| 7,270,188 B2 | 9/2007 | Cook et al. |
| 7,575,590 B2 | 8/2009 | Watson |
| 7,600,956 B2 | 10/2009 | McDuff et al. |
| 7,635,034 B2 | 12/2009 | Williams |
| 7,670,369 B2 | 3/2010 | Schaeffer |
| 7,682,383 B2 | 3/2010 | Robin |
| 7,752,969 B2 | 7/2010 | Stevens |
| 7,758,367 B2 | 7/2010 | Siebens et al. |
| 2001/0025195 A1* | 9/2001 | Shaolian et al. ............. 623/1.13 |
| 2002/0032479 A1* | 3/2002 | Hankh et al. ............. 623/1.16 |
| 2002/0052643 A1* | 5/2002 | Wholey et al. ............. 623/1.13 |
| 2003/0144725 A1* | 7/2003 | Lombardi ................... 623/1.13 |
| 2003/0195609 A1 | 10/2003 | Berenstein et al. |
| 2004/0059406 A1 | 3/2004 | Cully et al. |
| 2004/0106972 A1 | 6/2004 | Deaton |
| 2004/0106978 A1 | 6/2004 | Greenberg et al. |
| 2005/0055082 A1* | 3/2005 | Ben Muvhar ............ A61F 2/91 623/1.15 |
| 2005/0131519 A1 | 6/2005 | Hartley |
| 2005/0149166 A1 | 7/2005 | Schaeffer et al. |
| 2005/0267568 A1 | 12/2005 | Berez et al. |
| 2006/0206200 A1 | 9/2006 | Garcia et al. |
| 2006/0206201 A1 | 9/2006 | Garcia et al. |
| 2006/0229704 A1 | 10/2006 | Thistle et al. |
| 2006/0287704 A1 | 12/2006 | Hartley |
| 2007/0088425 A1 | 4/2007 | Schaeffer |
| 2007/0173921 A1 | 7/2007 | Wholey et al. |
| 2007/0219621 A1 | 9/2007 | Hartley et al. |
| 2007/0225797 A1 | 9/2007 | Krivoruhko |
| 2007/0244542 A1 | 10/2007 | Greenan et al. |
| 2008/0228256 A1 | 9/2008 | Erickson et al. |
| 2008/0262595 A1 | 10/2008 | Chu et al. |
| 2009/0030502 A1 | 1/2009 | Sun et al. |
| 2009/0149939 A1 | 6/2009 | Godlewski et al. |
| 2009/0259290 A1 | 10/2009 | Bruszewski et al. |
| 2009/0270971 A1 | 10/2009 | Xiao |
| 2009/0270974 A1 | 10/2009 | Berez et al. |
| 2009/0275974 A1 | 11/2009 | Marchand et al. |
| 2009/0287288 A1 | 11/2009 | Berez et al. |
| 2009/0292348 A1 | 11/2009 | Berez et al. |
| 2009/0319017 A1 | 12/2009 | Berez et al. |
| 2010/0010624 A1 | 1/2010 | Berez et al. |
| 2010/0057186 A1 | 3/2010 | West et al. |
| 2010/0082091 A1 | 4/2010 | Berez et al. |
| 2010/0100055 A1 | 4/2010 | Mustapha |
| 2010/0121429 A1 | 5/2010 | Greenan et al. |
| 2010/0168837 A1 | 7/2010 | Magnuson et al. |

FOREIGN PATENT DOCUMENTS

| | | |
|---|---|---|
| WO | 2005/007219 | 1/2005 |
| WO | 2006/124824 | 11/2006 |
| WO | 2007/028112 | 3/2007 |
| WO | 2008/021555 | 2/2008 |
| WO | WO-2008021557 A1 | 2/2008 |
| WO | 2008/042270 | 4/2008 |
| WO | 2008/057568 | 5/2008 |
| WO | 2008/062405 | 5/2008 |
| WO | 2008/112415 | 9/2008 |
| WO | 2009/017632 | 2/2009 |
| WO | 2009/052432 | 4/2009 |
| WO | 2009/082718 | 7/2009 |
| WO | 2009/134686 | 11/2009 |
| WO | WO-2010024879 A1 | 3/2010 |
| WO | 2011/047004 | 4/2011 |

* cited by examiner

DEVICES AND METHODS FOR IN SITU FENESTRATION OF A STENT-GRAFT AT THE SITE OF A BRANCH VESSEL

CROSS REFERENCE TO RELATED APPLICATIONS

This application is a non-provisional of, and claims priority to, U.S. Provisional Patent Application No. 61/414,065, entitled "Devices and Methods For in situ Fenestration of a Stent-Graft at the Site of a Branch Vessel," filed Nov. 16, 2010, which is hereby incorporated by reference in its entirety.

BACKGROUND

Field

The present disclosure generally relates to stent-grafts for treating diseases of the vasculature.

Discussion of the Related Art

Stent-grafts are medical devices constructed to reinforce, replace, or bridge, a part of a damaged, unhealthy, or diseased blood vessel. A stent-graft may thus guide blood flow through a lumen defined by its cylindrical interior. Where a stent-graft is implanted in a patient's body, however, blood is typically not permitted to leak or flow over an exterior portion of the stent-graft.

Occasionally, a stent-graft may be placed in a part of a patient's body such that it occludes or blocks one or more side-branch vessels (i.e., vessels that join the main vessel within which the stent-graft is implanted). For instance, patients who develop abdominal aortic aneurysms ("AAAs") are often implanted with stent-grafts. During a procedure of this type, a stent-graft may be implanted in a patient's abdominal aorta. However, such a stent-graft may partially or fully occlude blood flow to a patient's renal arteries, which branch away from the patient's abdominal aorta.

Commonly, in order to direct blood flow to a patient's side-branch vessels, stent-grafts, which may otherwise occlude these vessels, are manufactured with, or altered in situ to include, a fenestration or window near a location of one or more side-branch vessels. Thus, in operation, blood may escape through the fenestration and into one or more side-branch vessels.

Fenestrated stent-grafts have been manufactured with their fenestrations opened a priori of surgical implantation. More particularly, fenestrated stent-grafts have been manufactured as pre-sized commercial off the shelf components as well as more customized components fenestrated based upon preoperative anatomic information (e.g., imaging data collected via x-ray systems, etc.) In either instance, however, a fenestrated stent-graft may fit poorly within a patient's anatomy (either due to the pre-sized nature of the device and/or as a result of inadequate or imprecise preoperative anatomic data). Likewise, where stent-grafts have been fenestrated in situ, it has been similarly challenging to adjust the orientation of such stent-grafts to align with various anatomies.

In light of these shortcomings, physicians have struggled to ensure alignment between the fenestrations made in stent-grafts and the branch-vessels into which these fenestrations will ultimately direct blood flow. For example, until now, alignment has been accomplished (and/or attempted) largely through the use of multiple guidewires as well as, in some instances, an angiographic catheter. These measures have been necessary, because stent-grafts, as described above, may fit only poorly into their respective anatomies. Moreover, where stent-grafts have been implanted near side-branch vessels, physicians have struggled, prior to alignment of one or more fenestrations with these vessels, with occlusion by the stent-graft of these vessels.

A more suitable fenestrated stent-graft is therefore desirable. More particularly, a stent graft suited to more careful placement in a patient's anatomy is desirable. A need similarly exists for the reduction of surgical equipment in a patient's anatomy. Likewise, there is a need for a stent-graft that does not occlude side-branch vessels prior to alignment.

SUMMARY

The present disclosure includes a stent-graft comprising a first portion that is configured to engage a vessel wall, a second portion that is configured not to engage the vessel wall, and a perfusion window that is configured to permit blood flow. The stent-graft may further comprise a transition portion between the first portion and the second portion, and the perfusion window may be formed in the first portion, the second portion, and/or the transition portion. In a variety of embodiments, one of the first and the second portion may have a smaller diameter than the other. Similarly, in a variety of embodiments, the transition portion may be frustoconically shaped.

Further, and in various embodiments, the stent-graft may comprise a fenestratable target portion that is fenestratable in such a manner that it can receive a side-branch stent-graft. The target portion may be visible in situ in the presence of a contrast media that perfuses through the perfusion window. More particularly, a fenestration device that fenestrates a target portion of the stent-graft and facilitates the installation of a side-branch stent-graft. In various embodiments, the stent-graft may be deployable for treating an iliac artery. An occluder may be provided that blocks the perfusion window.

BRIEF DESCRIPTION OF THE DRAWINGS

The features and advantages of the present disclosure will become more apparent from the detailed description set forth below when taken in conjunction with the drawings.

DETAILED DESCRIPTION OF THE ILLUSTRATED EMBODIMENTS

Figure 1:
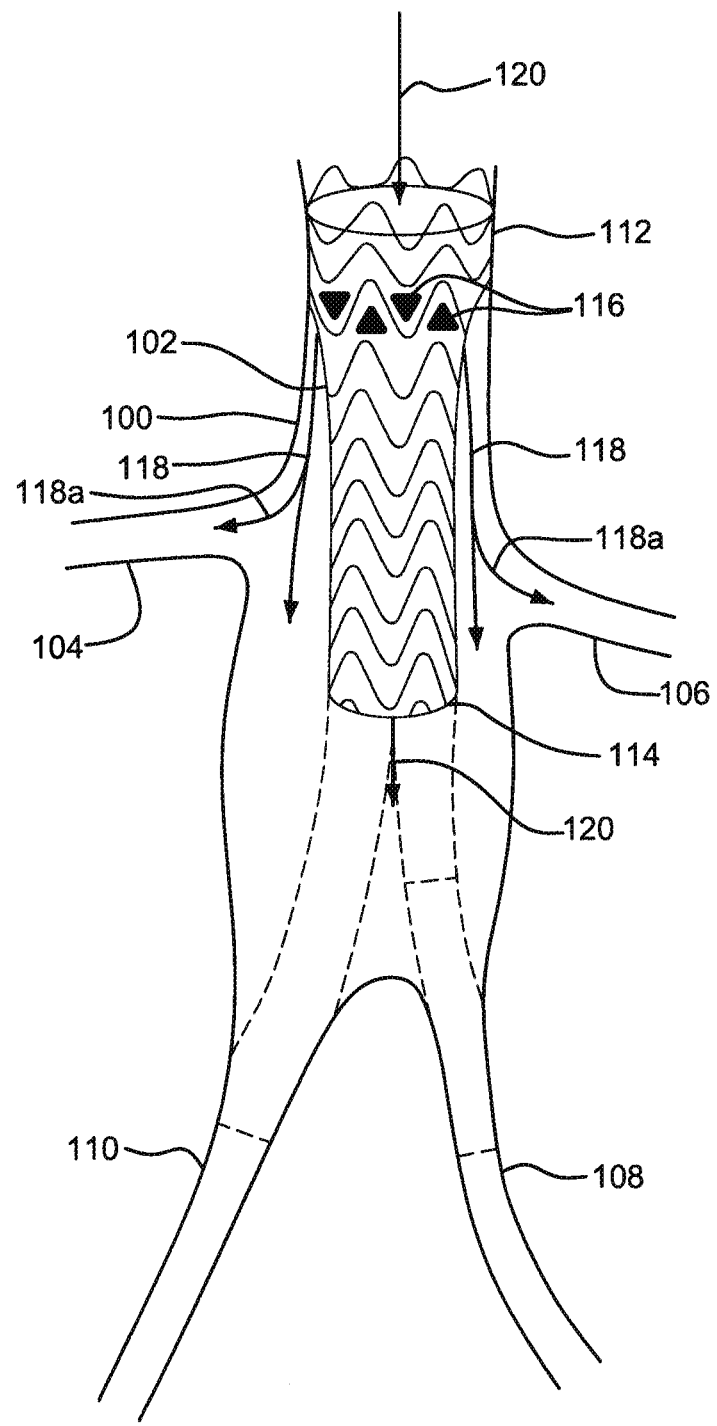
FIG. 1 illustrates an embodiment of a stent-graft deployed in a vessel.

Persons skilled in the art will readily appreciate that various aspects of the present disclosure may be realized by any number of methods and apparatuses configured to perform the intended functions. Stated differently, other methods and apparatuses may be incorporated herein to perform the intended functions. It should also be noted that the accompanying drawing figures referred to herein are not all drawn to scale, but may be exaggerated to illustrate various aspects of the present disclosure, and in that regard, the drawing figures should not be construed as limiting. Finally, although the present disclosure may be described in connection with various principles and beliefs, the present disclosure should not be bound by theory.

Throughout this specification and in the claims, the term "distal" may refer to a location that is, or a portion of an intraluminal device (such as a stent-graft) that when implanted is, further downstream with respect to blood flow than another portion of the device. Similarly, the term "distally" may refer to the direction of blood flow or further downstream in the direction of blood flow.

The term "proximal" may refer to a location that is, or a portion of an intraluminal device that when implanted is, further upstream with respect to blood flow. Similarly, the term "proximally" may refer to the direction opposite to the direction of blood flow or upstream from the direction of blood flow.

With further regard to the terms proximal and distal, and because the present disclosure is not limited to peripheral and/or central approaches, this disclosure should not be narrowly construed with respect to these terms. Rather, the devices and methods described herein may be altered and/or adjusted relative to the anatomy of a patient.

The terms "branch vessel," "side-branch" and/or "side-branch vessel" may refer to a vessel that branches off from a main vessel. For example, "branch vessels" of the thoracic and abdominal arteries include, but are not limited to, the celiac, inferior phrenic, superior mesenteric, lumbar, inferior mesenteric, middle sacral, middle suprarenal, renal, internal spermatic, ovarian (in the female), innominate, left carotid, and left subclavian arteries. As another example, the hypogastric artery is a branch vessel of the common iliac, which is a main vessel in this context. Thus, it should be seen that "branch vessel" and "main vessel" are relative terms.

While the specific embodiments are described in greater detail below, in general, the present disclosure will focus primarily upon devices and methods for treating disease of the ascending aorta, aortic arch, and descending aorta; however, these devices and methods may be applied to other diseases of the vasculature, including, for example, any disease where a larger vessel and one or more branch vessels are to be treated.

A stent-graft in accordance with various embodiments may have a first portion that is configured to engage a vessel wall and a second portion that is configured not to engage the vessel wall; and a perfusion window that is configured to permit blood flow. The stent-graft can include a transition portion between the first portion and the second portion. The perfusion window can be formed in one of the first portion, the second portion, and the transition portion. In various embodiments, one of the first and second portions of the stent-graft has a smaller diameter than the other. The stent-graft may include a transition portion between the first portion and the second portion that is frustoconically shaped.

A stent-graft in accordance with a number of embodiments can comprise a first portion that is configured to engage a vessel wall; and a second portion having a perfusion window through which blood flows in a first configuration and through which blood is prevented from flowing in a second configuration. The stent-graft can further include a transition portion between the first portion and the second portion. The perfusion window can be formed in one of the first portion, the second portion, and the transition portion. One of the first and second portions has a smaller diameter than the other. The transition portion between the first portion and the second portion that can be frustoconically shaped.

Thus, various embodiments may comprise a stent-graft having a first portion that is configured to engage a vessel wall, a second portion that is configured not to engage a vessel wall, and a perfusion window that is configured to permit blood flow. In various embodiments, a first portion may engage, for example, a portion of a patient's vessel (e.g., the patient's aorta), while a second portion may extend distally (and taper radially) into the vessel in such a way that it does not engage or make contact with the vessel wall. Further, and in various embodiments, the first portion may be separated from the second portion by a transition portion, which may itself comprise one or more perfusion windows.

A perfusion window may permit blood and/or other fluids to flow from a region interior to the first portion of a stent-graft to a region exterior to the second portion of the stent-graft. For example, a perfusion window may, in various embodiments, permit blood, as well as one or more contrast media, to flow over an exterior surface of the second portion.

Contrast media may comprise, for example, fluoroscopic and/or radiopaque agents, dyes, and/or the like. With respect to contrast media, in general, these may be used to identify side-branch vessels (e.g., the renal arteries). More specifically, contrast media may be used to observe real time X-ray images of cardiovascular structures such as the renal arteries during implantation of a stent-graft. For example, contrast media may be permitted to flow through one or more perfusion windows and over a second portion of the stent-graft, whereupon fluoroscopic images of the contrast agent in the blood may be developed. These images may, in various embodiments, comprise still images and/or real time motion images. These images may further allow two-dimensional visualization, for example, of the location and/or anatomical disposition of a vessel (e.g., an aorta), any side-branch vessels (e.g., renal arteries), the second portion of the stent-graft (including, in various embodiments, a target portion of the stent-graft) and/or the prosthesis or stent-graft itself. Likewise, in various embodiments, one or more characteristics (e.g., location, orientation, etc.) of a stent-graft may be determined using one or more radiopaque or echogenic markers or indicators. These may be incorporated in or on the stent-graft. A radiopaque marker may comprise, in various embodiments, a radio-opaque element that enhances imaging and/or detection during and/or following delivery or deployment of the stent-graft. Radiopaque markers may comprise one or more of tungsten, gold, platinum, and/or any other material or combination of materials that is visible or detectable in the presence of radiation.

Having visualized one or more vessels, the location and/or orientation of a stent-graft implanted in one or more of the vessels, and/or a portion of the stent-graft, a physician may use a fenestration device to make a fenestration, in situ, in one or more portions of an implanted stent-graft. For instance, a physician may fenestrate a stent-graft in a location that is proximate to and/or spans a patient's side-branch vessel or vessels (e.g., one or more renal arteries). Moreover, after a stent-graft is fenestrated, a physician may deliver and/or implant one or more side-branch stent-grafts, which may be coupled to the stent-graft at the one or more points of fenestration. Thus, a patient may be implanted with a first stent-graft, which may be visualized and fenestrated in situ, as well as one or more side-branch stent-grafts, which may be coupled to one or more points of fenestration.

With respect to FIG. 1, a stent-graft 102 having a proximal end 112 and a distal end 114 is shown implanted in an aorta 100. More particularly, in FIG. 1, stent-graft 102 is shown positioned in aorta 100 proximal to iliac arteries 108 and 110. In various embodiments, however, and as described elsewhere herein, stent-graft 102 may be implanted in any vessel (e.g., any main vessel) in a patient's body that includes one or more branch vessels.

Figure 2:
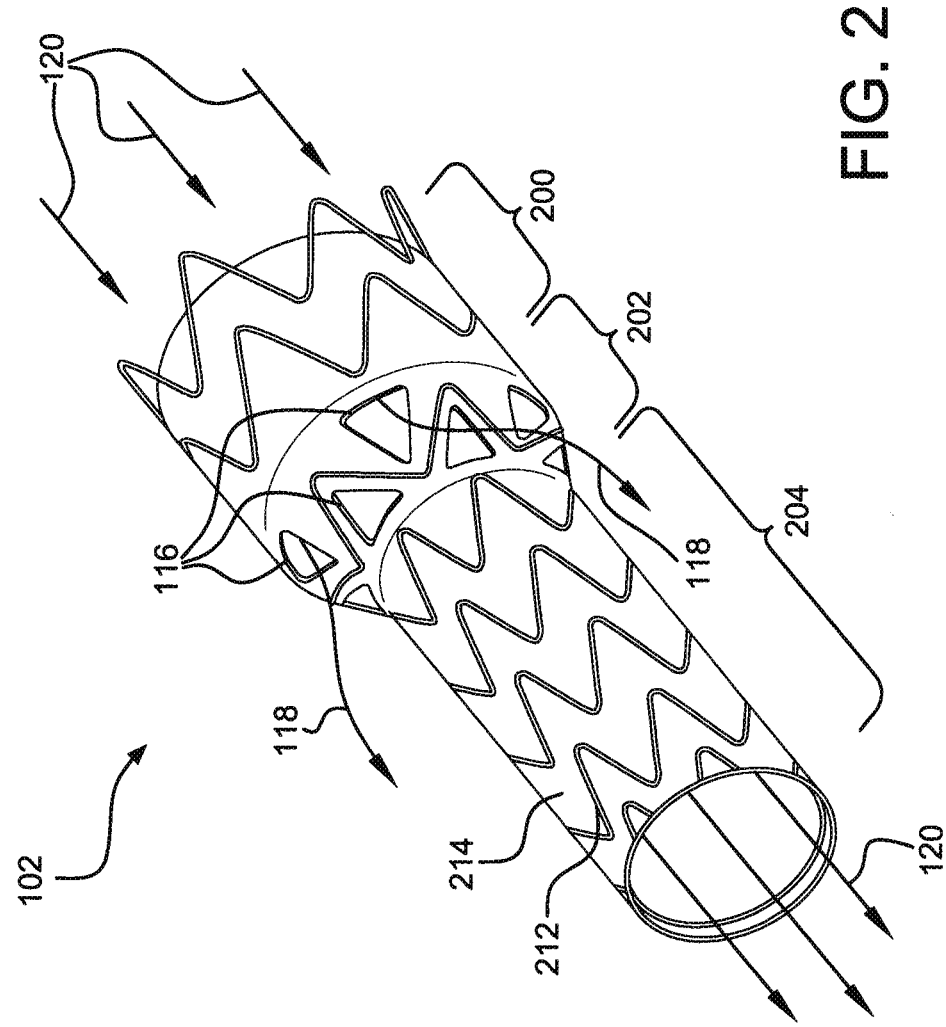
FIG. 2 illustrates a perspective view of a stent-graft.

With respect to FIG. 2, a perspective view of stent-graft 102 is shown. Stent-graft 102 may be divided into a plurality of sections or portions 200, 202 and 204. A first section 200 may comprise a larger diameter capable of engaging a vessel 100 wall. Engagement of a vessel 100 wall may hold stent-graft 102 in place so as to prevent movement of stent-graft 102 once it is deployed within vessel 100. In various embodiments, first section 200 may engage vessel 100 by way of a friction fit, one or more hooks, one or more barbs, and/or one or more raised stent apices, which may assist in fastening or adhering stent-graft 102 to vessel 100.

A transition section 202 may taper between first section 200 and smaller diameter second section 204. Transition section 202 may comprise at least one perfusion window 116, through which blood and/or other fluids (e.g., contrast media) may flow or perfuse. A direction and manner of fluid flow through perfusion windows 116 is depicted by arrows 118. Although perfusion windows 116 are depicted in the Figures as triangles, perfusion windows 116, may, in various embodiments, comprise any shape, e.g., circles, ovals, rectangles, squares, diamonds, polyhedrons, combinations of any of these, and the like. Perfusion windows 116 may be further manufactured by any method known in the art including using a laser to cut perfusion windows 116 through stent-graft 102.

Second section 204 may comprise a smaller diameter than first section 200. And, as described elsewhere herein, second section 204 may be configured to not engage vessel 100 wall. For instance, second section 204 may be smaller in diameter than either of first section 200 and/or transition section 202. Thus, second section 204 does not engage vessel 100 wall, because it is spaced apart therefrom.

For a stent-graft 102 having the above described configuration, blood may perfuse through perfusion windows 116 and continue to flow into branch vessels 104 and 106 (i.e., prior to fenestration, as described elsewhere herein). Blood exiting perfusion windows 116 may further flow toward, for example, iliac arteries 108 and 110. Further, as used elsewhere herein, where stent-graft 102 is implanted in a main vessel (see above) and/or configured with perfusion windows 116 and/or three sections 200, 202, 204, stent-graft 102 may be referred to as a primary stent-graft (as opposed, for example, to a side-branch stent-graft).

In operation, stent-graft 102 may be deployed in a vessel 100 that comprises or meets with at least one branch vessel 104 and/or 106. For example, stent-graft 102 may be deployed proximate to and/or spanning one or more branch vessels 104 and/or 106. More particularly, first section 200 of stent-graft 102 may be deployed proximate to and/or spanning one or both of branch vessels 104 and/or 106. Second section 204, which may have a smaller diameter than first section 200, may not fully (or partially) engage a wall of vessel 100. Therefore, as blood flows into stent-graft 102, as illustrated by arrow 120, blood may flow through stent-graft 102, from proximal end 112 to distal end 114. As blood continues to flow in this direction, some blood may be diverted through perfusion windows 116. This feature of stent-graft 102 may permit blood to continue to flow in the space between stent-graft 102 and vessel 100. That is blood may perfuse through perfusion windows 116 so that it flows between second section 204 and vessel 100. Further, as mentioned above, as blood flows over the exterior surface of second section 204, some may be diverted or perfuse branch vessels 104 and/or 106, as illustrated by arrows 118a.

In a variety of embodiments, contrast media may be delivered to proximal end 112 and/or distal end 114 of stent-graft 102 such that the contrast media passes into and/or mixes with the blood stream. Contrast media may, in addition, be delivered systemically into a patient's body. As blood carries the contrast media, some of the blood containing contrast media may be diverted into and through perfusion windows 116 and into the space between second section 204 and vessel 100. More distally, and as blood continues to flow through the area between stent-graft 102 and vessel 100, some of the blood and contrast media may be diverted into branch vessels 104 and/or 106. A physician may, using a variety of fluoroscopic imaging techniques, detect the contrast media in a patient's branch vessels 104 and/or 106 in situ. In other words, a physician may take advantage of contrast media perfusing through perfusion windows 116 to image a portion of a patient's vasculature and/or a location, placement, and/or orientation of stent-graft 102, in situ. Likewise, in various embodiments, one or more characteristics (e.g., location, orientation, etc.) of stent-graft 102 may be determined using one or more radiopaque or echogenic markers or indicators. These may be incorporated in or on stent-graft 102.

Further, in various embodiments, a contrast media may illuminate or make visible one or more target portions of stent-graft 102. A target portion may comprise, for example, an area of stent-graft 102 that is located proximate to and/or spanning one or more side-branch vessels and/or a portion of stent-graft 102 that is more easily fenestratable than, for example, a sturdier or more durable portion of stent-graft 102. In various embodiments, a target portion may comprise a softer graft material and/or a graft material that is more visible, brighter, or otherwise distinguishable in the presence of a contrast media. For example, a target portion may comprise one or more radiopaque or echogenic markers or indicators. Having visualized stent-graft 102, a physician may utilize the variety of detailed information obtained about stent-graft 102 (e.g., information about a patient's vasculature and/or the location, placement, orientation, and/or characteristics of stent-graft 102), to manipulate, in great detail, stent-graft 102 (e.g., relative to, for example, the position or location of a patient's branch vessels 104 and/or 106).

Figure 3:
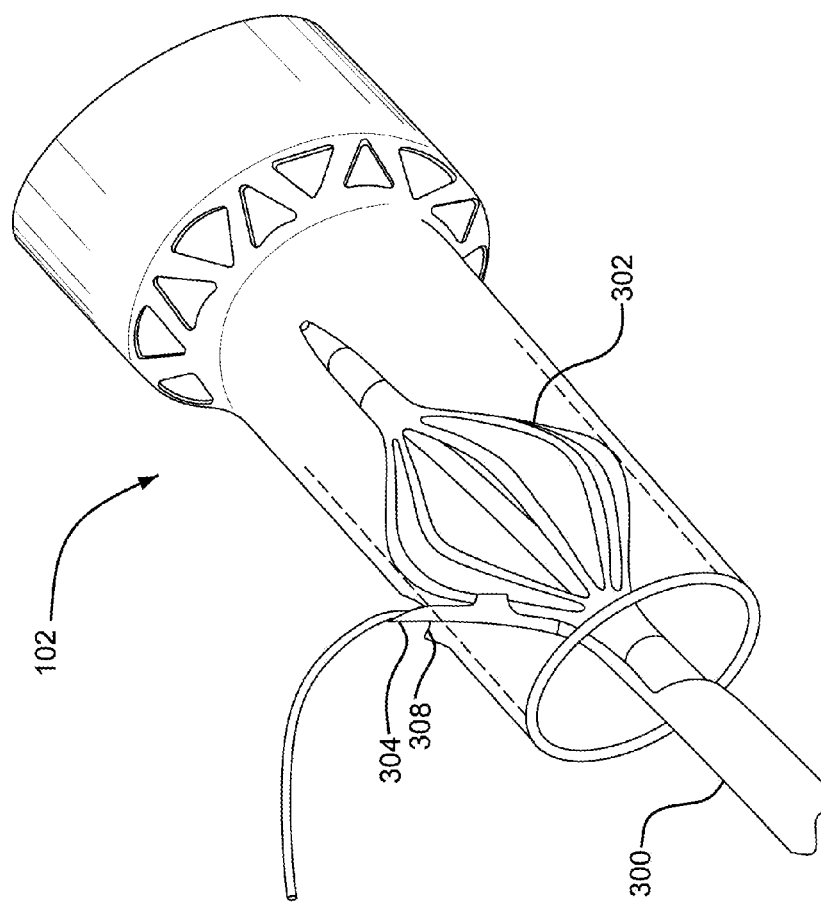
FIG. 3 illustrates a perspective view of a stent-graft and a fenestration tool within the stent-graft.

Turning now to FIG. 3, once stent-graft 102 is deployed and side-branch vessels 104 and 106 are visualized, as described above, a physician may insert a fenestration tool or device 300 to fenestrate stent-graft 102 at the location of one or more branch vessels 104 and/or 106 and/or at one or more target portions 308. As described elsewhere herein, a patient's side-branch vessels 104 and/or 106 as well as a placement of stent-graft 102 relative to the patient's side-branch vessels 104 and/or 106 may be carefully and precisely visualized. Thus, a physician may more accurately fenestrate stent-graft 102 in one or more locations proximate to one or more side-branch vessels 104 and/or 106 to attach one or more side-branch stent-grafts, as described more fully below. To this end, in various embodiments, fenestration device 300 may comprise a locating or centering tool 302, which may center, locate and/or engage a tip 304 of fenestration device 300 as well as provide leverage or a counter-force, so that tip 304 can be pushed through, or make a fenestration in, a side wall of stent-graft 102.

Accordingly, once stent-graft 102 is fenestrated, one or more side-branch, or secondary, stent-grafts may be delivered and deployed within one or more side-branch vessels 104 and/or 106. For example, and with particular reference to FIGS. 6 and 7, a portion of a side-branch stent-graft 400 may be deployed within a side-branch vessel 104 and/or 106. Further, during deployment, a portion of side-branch stent-graft 400 may be attached or coupled to stent-graft 102. That is, for example, a portion of side-branch stent-graft 400 may be coupled to stent-graft 102 via, or through, one or more of the fenestrations made by fenestration device 300. Moreover, in certain embodiments, after fenestration of stent-graft 102, a balloon may be placed in the fenestration and inflated to further define and/or widen the fenestration before deploying side-branch stent-graft 400.

Thus, one or more side-branch stent-grafts 400 may be precisely deployed within the vasculature of a patient. Each side-branch stent-graft 400 may be fastened or attached to stent-graft 102 at a fenestration point, which may be cut or made in situ based upon imaging data collected by a physician through the introduction of a contrast media in the patient's vasculature. That is, and in other words, side-branch stent-graft 400 may be attached, based upon imaging data, to stent-graft 102 precisely at a location of a patient's side-branch vessels 104 and/or 106. Further, side-branch stent-graft 400 may be inserted in a patient's vasculature and coupled to stent-graft 102 using only a single fenestration device 300. Thus, the disclosed devices and methods comprise a significant advantage over prior art devices and methods, which may not be fenestrated in situ to accommodate a patient's actual anatomy, which require, due to their inherent imprecision, a plurality of (e.g., percutaneous) installation devices (e.g., guidewires, catheters, and the like), and which may occlude a patient's side-branch vessels 104 and/or 106 during implantation.

Figure 4:
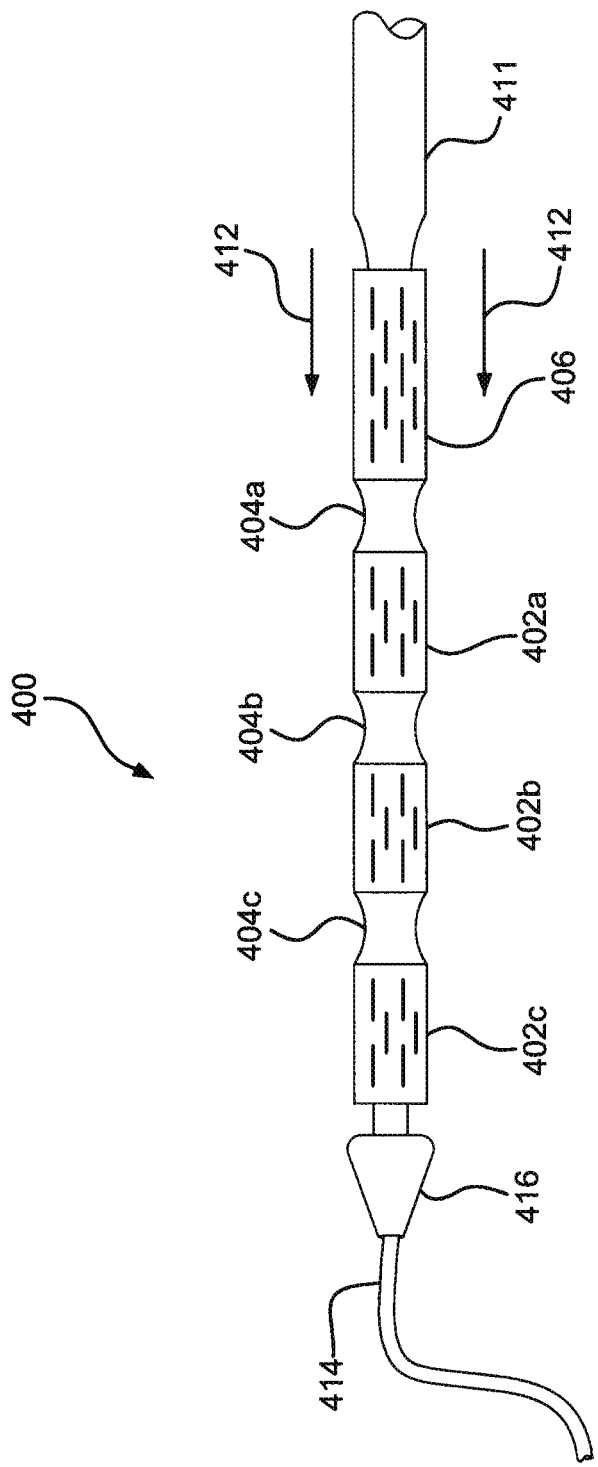
FIG. 4 illustrates a side view of a side-branch stent-graft mounted and constrained on a delivery catheter.
Figure 5:
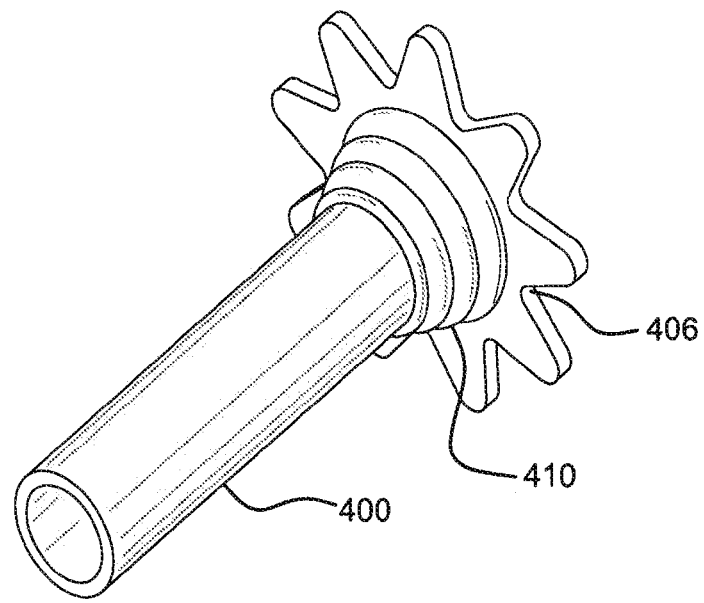
FIG. 5 illustrates a perspective view of a side-branch stent-graft when deployed.
Figure 6:
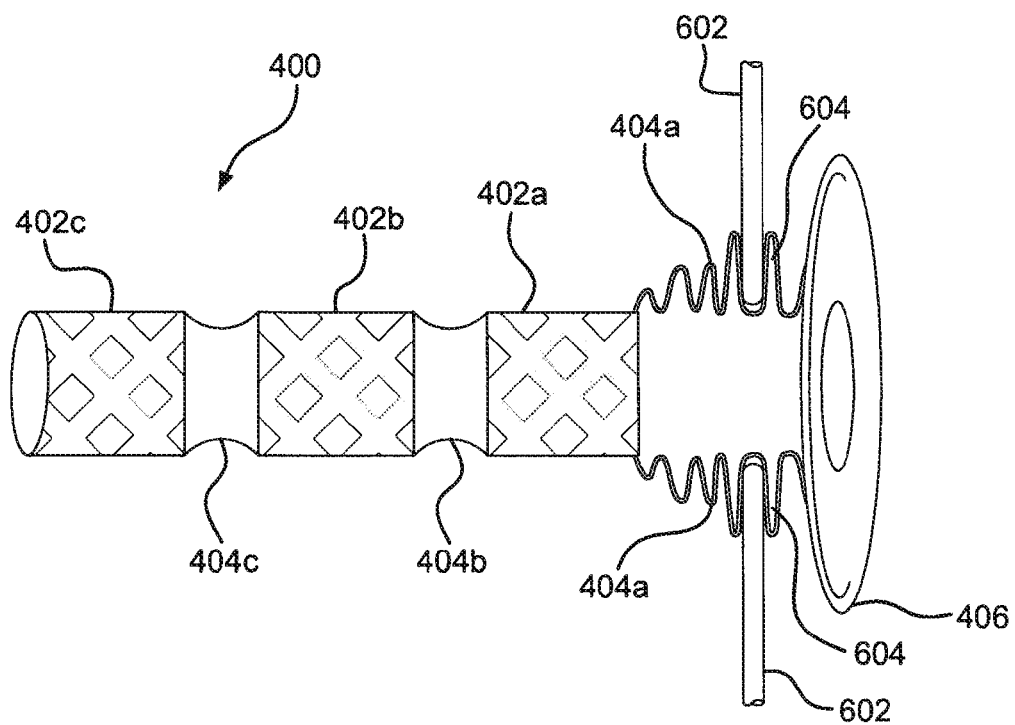
FIG. 6 illustrates a side view of a side-branch stent-graft when deployed against the wall of a stent-graft.
Figure 7:
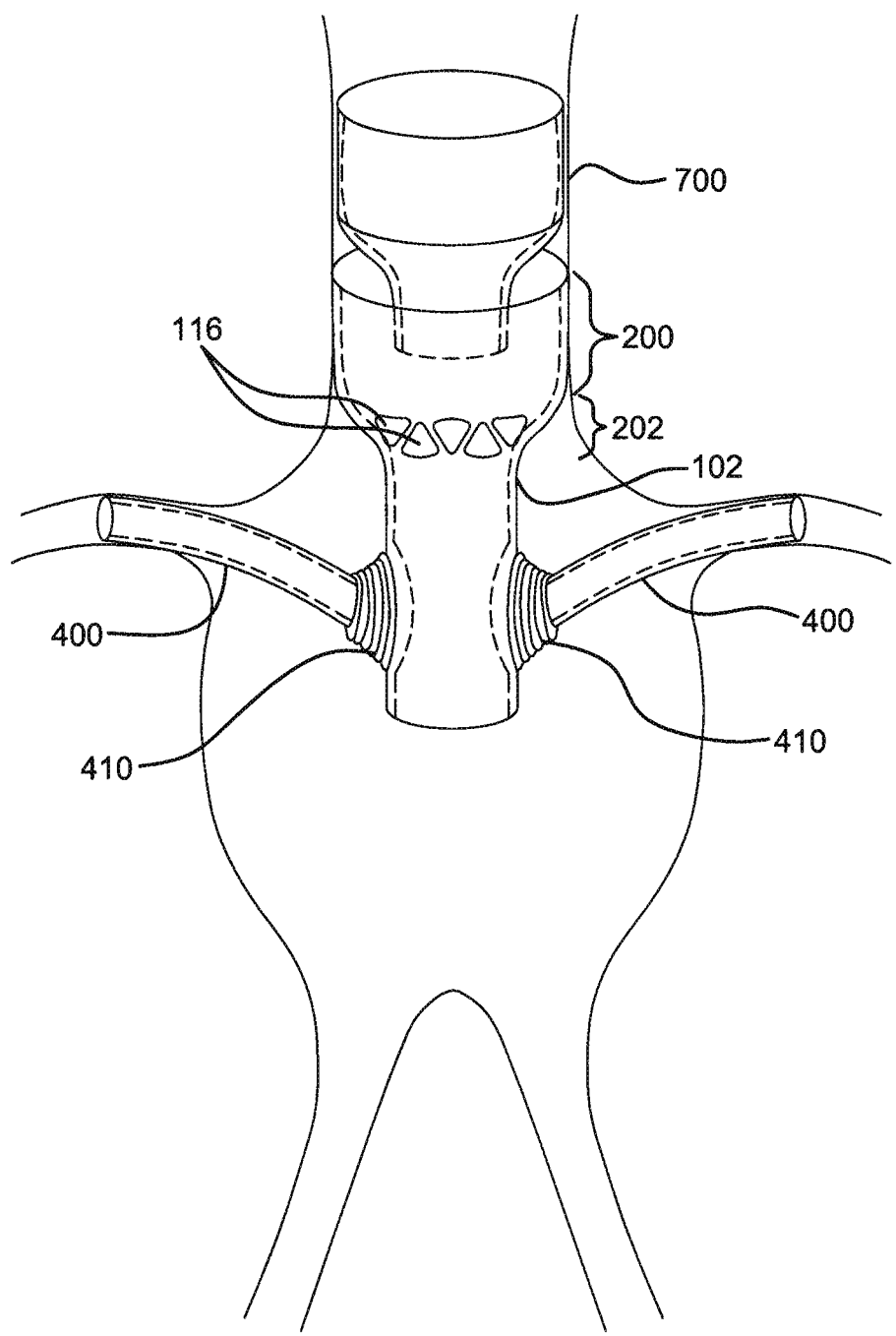
FIG. 7 illustrates a fully assembled modular stent-graft including an occluder that blocks a plurality of perfusion windows.

Broadly, and with particular reference now to FIGS. 4, 5, and 6, side-branch stent-graft 400 is depicted from a variety of perspectives and in a variety of configurations. For instance, with respect to FIG. 4, side-branch stent-graft 400 is depicted in a restrained configuration on a delivery catheter 411. Delivery catheter 411 may comprise an olive 416 and/or a guidewire 414. In a restrained configuration, side-branch stent-graft 400 may further comprise a restraining sleeve, which may isolate or constrain side-branch stent-graft 400 in a restrained or constrained configuration.

With particular reference to FIG. 4, and in various embodiments, side-branch stent-graft 400 may comprise a plurality of stent and/or stent-graft members 402a, b, c and/or 406. One or more graft members 404a, b, c may interconnect one or more stent members 402a, b, c and/or 406. For example, stent members 402a, b, c and/or 406 may comprise stent rings, and these may be interconnected by graft sections 404a, b, c. This construction allows for a highly flexible side-branch stent-graft 400 (because graft sections 404a, b, c may comprise a flexible material, such as ePTFE). Notwithstanding this construction, however, a variety of other constructions, as described herein and/or as known in the art, may be used. Further, and in a variety of embodiments, additional graft material and/or a cuff may be loosely placed on or coupled to at least a portion of an outer surface of stent member 402a, b, c, 406 and/or graft section 404a, b c.

Continuing, and with reference to FIGS. 5 and 6, side-branch stent-graft 400 is shown in an expanded configuration. As shown in FIG. 5, when side-branch stent-graft 400 is expanded, stent member 406 may expand to form a flat disc shape (which may comprise, for example, a covered or uncovered wire frame). In addition, as stent member 406 expands, graft 404a, b, c and/or a cuff (which may comprise loosely placed graft material) may "scrunch" or move in the direction indicated by arrows 412 (see FIG. 4).

This "scrunching" may form folds extending radially outward in the graft material of graft 404a, b, c and/or the cuff. These folds may, in turn, help to seal side-branch stent-graft 400 against a wall 602 of stent-graft 102 through which fenestration device 300 has made a fenestration 604 or puncture. That is, and with attention to FIG. 6, stent member 406 may form a flange-type seal as it lays flat against wall 602 of stent-graft 102. In this configuration, and in various embodiments, no blood, or only a minimum amount of blood, may leak through the fenestration 604. In addition, after graft 404a, b, c and/or the material comprising the cuff "scrunches" and forms folds, the folds may form on the outer and/or inner walls of stent-graft 102 to create an additional seal around fenestration 604.

In a variety of embodiments, once stent-graft 102 is fenestrated and one or more secondary stent-grafts 400 are delivered and deployed, it may be advantageous to block or otherwise occlude perfusion windows 116. Accordingly, with reference now to FIG. 7, a "window cover" or occluder 700 may be delivered to and/or deployed in stent-graft 102. More particularly, occluder 700 may be deployed interior to or within first section 200 and/or interior to or within transition section 202 of stent-graft 102 to block or occlude perfusion windows 116. Occluder 700 may, in various embodiments, have generally the same shape as first section 200 and/or transition section 202 of stent-graft 102. That is, occluder 700 may conform to an interior surface of stent-graft 102. However, occluder 700 does not have perfusion windows. Indeed, occluder 700 may comprise a solid or impermeable wall, which covers and/or occludes perfusion windows 116 entirely or in part.

With regard to delivery and deployment of occluder 700, occluder 700 may be delivered in a constrained configuration and expanded within stent-graft 102. Occluder 700 may be further released from a constrained position within stent-graft 102 to seal or occlude perfusion windows 116. Thus, in a deployed configuration, occluder 700 may force or constrain blood to flow only though stent-graft 102 and/or one or more side-branch stent-grafts 400.

Thus, in various embodiments, a method for in situ fenestration of a stent-graft 102 at the site of one or more side-branch vessels 104 and/or 106 is disclosed. The method may comprise deploying stent-graft 102 within a vessel 100, in which the stent-graft 102 spans and/or extends at least partially distal to one or more side-branch vessels 104 and/or 106. In various embodiments, the method may further comprise deploying at least one side-branch stent-graft 400 in at least one side-branch vessel 104 and/or 106 after fenestrating stent-graft 102. Further still, the method may comprise covering at least one perfusion window 116 with an occluder 700, which may comprise, in various embodiments, a stent-graft and/or a graft and/or graft material. In various embodiments, stent-graft 102 and/or side-branch stent-graft 400 may comprise a polymer, such as ePTFE, one or more self-expanding stents, a titanium-nickel alloy (e.g., nitinol), one or more stents with undulations, and the like. Further, in various embodiments, and as described elsewhere herein, the shape of one or more perfusion windows 116 may comprise a triangle, a circle, an oval, a rectangle, a square, a diamond, a polyhedron, combinations of these, and the like. Moreover, and in various embodiments, first section 200 of stent-graft 102 may comprise hooks, barbs and/or raised stent apices that assist in fastening and/or adhering stent-graft 102 to vessel 100.

Returning briefly to FIG. 2, a graft 214 comprising any of the grafts and/or stent-grafts described above may be made up of any material which is suitable for use as a graft in the chosen body lumen. A graft 214 may comprise one or a variety of materials. Furthermore, a graft 214 may comprise multiple layers of material, which can be the same material or different material. Although a graft 214 may have several layers of material, the graft may have a layer that is formed into a tube (innermost tube) and an outermost layer that is formed into a tube (outermost tube). In some embodiments, a graft 214 may be fenestrated with a fenestration tool.

Many graft materials are known, and in various embodiments, these materials can be used in combination and assembled together to comprise a graft. These materials may be further extruded, coated and/or formed from wrapped films, and/or a combination thereof. Polymeric materials, biodegradable materials, and/or natural materials can be used for specific applications.

In various embodiments, a graft may comprise synthetic polymers including nylon, polyacrylamide, polycarbonate, polyformaldehyde, polymethylmethacrylate, polytetrafluoroethylene, polytrifluorochlorethylene, polyvinylchloride, polyurethane, elastomeric organosilicon polymers, polyethylene, polypropylene, polyurethane, polyglycolic acid, polyesters, polyamides, their mixtures, blends, and copolymers. In a variety of embodiments, a graft may be made from a class of polyesters such as polyethylene terephthalate including DACRON® and MYLAR® and polyaramids such as KEVLAR®, polyfluorocarbons such as polytetrafluoroethylene (PTFE) with and without copolymerized hexafluoropropylene (TEFLON® or GORE-TEX®), and porous or nonporous polyurethanes. Further, in a variety of embodiments, a graft may comprise expanded fluorocarbon polymers (especially PTFE), materials described in British. Pat. Nos. 1,355,373; 1,506,432; or in U.S. Pat. Nos. 3,953,566; 4,187,390; or 5,276,276, all of which are incorporated by reference in their entireties.

In various embodiments, fluoropolymers may include polytetrafluoroethylene (PTFE), expanded PTFE (ePTFE), fluorinated ethylene propylene (FEP), copolymers of tetrafluoroethylene (TFE) and perfluoro (propyl vinyl ether) (PEA), homopolymers of polychlorotrifluoroethylene (PCTFE), and its copolymers with TFE, ethylene-chlorotrifluoroethylene (ECTFE), copolymers of ethylene-tetrafluoroethylene (ETFE), polyvinylidene fluoride (PVDF), and polyvinylfluoride (PVF). In various embodiments, a graft may comprise any combination of the materials listed above. Further, in various embodiments, a graft may be substantially impermeable and/or permeable to bodily fluids. A substantially impermeable graft may be made from materials that are substantially impermeable to bodily fluids or can be constructed from permeable materials treated or manufactured to be substantially impermeable to bodily fluids (e.g. by layering different types of materials described above or known in the art). In various embodiments, stent-graft 102, side-branch stent-graft 400 and/or occluder 700, as described above, may be made from any combination of the materials described above, including ePTFE.

Any stent, including stent 212 and/or stent members 402a, b, c, and/or 406, as described elsewhere herein, may be generally cylindrical when restrained and/or when unrestrained and may comprise helically arranged undulations having a plurality of helical turns. In a variety of embodiments, undulations may be aligned so that they are "in-phase" with each other, as shown, for example, in FIG. 1. More specifically, undulations may comprise apices in opposing first and second directions. When these undulations are in-phase, apices in adjacent helical turns are aligned so that apices can be displaced into respective apices of a corresponding undulation in an adjacent helical turn. In certain embodiments, undulations may have a sinusoidal shape, a U shape, a V shape, and/or an ovaloid shape, as described in U.S. Pat. No. 6,042,605, both of which are incorporated by reference herein in their entireties.

In various embodiments, a stent may be fabricated from a variety of biocompatible materials including commonly known materials (or combinations of materials) used in the manufacture of implantable medical devices. Such materials may include 316L stainless steel, cobalt-chromium-nickel-molybdenum-iron alloy ("cobalt-chromium"), other cobalt alloys such as L605, tantalum, nitinol, or other biocompatible metals. In some embodiments, any stent and/or stent-graft described herein may comprise a balloon expandable stent and/or stent-graft and/or a self-expanding stent and/or stent-graft. Further, in certain embodiments, a stent may comprise a wire wound stent, which may or may not comprise undulations.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shape, size, and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein.

What is claimed is:

1. A stent-graft comprising:
   a stent-graft member including a stent and a graft, the graft defining a lumen for conveying blood flow, the stent-graft member including,
      a first portion having a first diameter that is configured to engage a vessel wall of a vessel, the vessel wall defining a vessel lumen,
      a second portion having a second diameter that is smaller than the first diameter of the first portion,
      a transition portion that has an interior surface and extends between the first portion and the second portion, and
      a perfusion window formed in the transition portion and oriented to permit blood flow through the transition portion and parallel to a longitudinal axis of the stent-graft member after deployment of the stent graft member in the vessel; and
   an occluder free of any perfusion windows, such that the occluder has a continuous, impermeable wall, the occluder having generally the same shape as an interior surface of the transition portion and being inserted into the stent-graft member to block the perfusion window without blocking flow through the lumen of the stent-graft member.

2. The stent-graft of claim 1, further comprising a target portion that is fenestratable to receive a side-branch stent-graft.

3. The stent-graft of claim 1, further comprising an iliac portion that couples to the second portion and is insertable into an iliac artery.

4. The stent-graft of claim 1, further comprising a target portion that is visible in situ in the presence of a contrast media that perfuses through the perfusion window.

5. The stent-graft of claim 1, wherein the stent-graft is configured to be fenestrated by a fenestration device and coupled to a side-branch stent-graft.

6. The stent-graft of claim 1, wherein the second portion of the stent-graft has a plurality of branch apertures each configured to receive a branch stent-graft, the stent-graft further comprising a plurality of branch stent-grafts received in respective ones of the plurality branch apertures, and further wherein the occluder is received in the body such that the occluder is engaged with the inner surface of the wall of the body such that substantially all blood entering the lumen of the body at the proximal end of the body passes through the lumen of the body out the distal end of the body and out of the branch stent-grafts without otherwise flowing through the wall of the body.

7. The stent-graft of claim 1, wherein the occluder conforms to the interior surface of stent-graft to block the perfusion window without interfering with blood flow through the lumen of the stent-graft member.

8. A stent-graft comprising:
a body including a stent structure and a graft structure, the body having a wall defining an outer surface and an inner surface forming a lumen, the body defining a proximal end and a distal end and including,
a first portion having a perfusion aperture through the wall of body that is oriented to permit blood flow along the outer surface of the body during deployment of the body in the vessel, and
a second portion having a plurality of branch apertures each configured to receive a branch stent-graft;
a plurality of branch stent-grafts received in respective ones of the plurality branch apertures; and
an occluder free of any perfusion windows, such that the occluder has a continuous, impermeable wall, the occluder being separate from the body and received in the body such that the occluder is engaged with the inner surface of the wall of the body to block flow through the perfusion aperture following deployment of the body such that substantially all blood entering the lumen of the body at the proximal end of the body passes through the lumen of the body out the distal end of the body and out of the branch stent-grafts without otherwise flowing through the wall of the body.

* * * * *